United States Patent [19]

Mueller

[11] 4,447,451

[45] May 8, 1984

[54] TREATMENT OF ADULT RESPIRATORY DISTRESS SYNDROME

[75] Inventor: Jerry C. Mueller, Kalamazoo, Mich.

[73] Assignee: The Upjohn Manufacturing Company M, Puerto Rico

[21] Appl. No.: 447,052

[22] Filed: Dec. 6, 1982

Related U.S. Application Data

[63] Continuation of Ser. No. 284,656, Jul. 20, 1981, abandoned.

[51] Int. Cl.³ .............................................. A61K 31/19
[52] U.S. Cl. .................................... 424/317; 424/308
[58] Field of Search ................................ 424/317, 308

[56] References Cited

U.S. PATENT DOCUMENTS

| | | | |
|---|---|---|---|
| 3,228,831 | 1/1966 | Nicholson et al. | 424/317 |
| 3,452,079 | 6/1969 | Shen et al. | 260/469 |
| 3,865,949 | 2/1975 | Grieg | 424/317 |

OTHER PUBLICATIONS

Goodman & Gilman, "The Pharmacological Basis of Therapeutics", 6th Ed., 1980, pp. 711–713.
Bone, Practical Cardiology, vol. 5, No. 2, (2–1979), pp. 49–63.

Primary Examiner—Leonard Schenkman
Attorney, Agent, or Firm—William G. Jameson; John J. Killinger

[57] ABSTRACT

A process for treating adult respiratory distress syndrome by the systemic administration of ibuprofen (p-isobutylhydratropic acid) or a salt or ester thereof. Dosage forms are also disclosed.

2 Claims, No Drawings

TREATMENT OF ADULT RESPIRATORY DISTRESS SYNDROME

This is a continuation of application Ser. No. 284,656, filed July 20, 1981, now abandoned.

BRIEF DESCRIPTION OF THE INVENTION

This invention is the new use for known compounds, ibuprofen, p-isobutylhydratropic acid, including the salts or esters thereof, have been found to be useful for treating adult respiratory distress syndrome by the systemic administratin of the compounds.

BACKGROUND OF THE INVENTION

Ibuprofen, its salt or esters, are known to be useful for treating a variety of medical conditions, including inflammation, arthritis, dental pain, reducing platelet adhesiveness and in coronary infarct.

"Shock lung" now known as the adult respiratory distress syndrome (ARDS) generally occurs following massive trauma; however, there are many other causes. The etiologies of this syndrome, its clinical aspects and means of preventing and treating ARDS are disclosed by Dr. Roger C. Bone, M.D. in Diagnosis and Management of Adult Respiratory Distress Syndrome; Practical Cardiology, Vol. 5, No. 2, pp. 49–63, February, 1979.

Dr. Bone discloses medicinal treatments with antibiotics, corticosteroids, and antacids.

DETAILED DESCRIPTION OF THE INVENTION

The active compounds of the present invention are ibuprofen (p-isobutylhydratropic acid) including the alkyl esters of from 1 to 8 carbon atoms, inclusive, including isomeric forms or the pharmacologically acceptable salts.

The esters can be the methyl, ethyl, propyl, isopropyl, butyl, isobutyl, tert-butyl, pentyl, and octyl esters.

Pharmacologically acceptable salts can be, for example, the alkali metal, alkaline earth and ammonium salts.

The compositions of the present invention are preferably presented for systemic administration to humans and animals in unit dosage forms, such as tablets, capsules, pills, powders, granules, suppositories, sterile parenteral solutions or suspensions, sterile non-parenteral solutions or suspensions, and oral solutions or suspensions and the like, containing suitable quantities of an active ingredient.

For oral administration either solid or fluid unit dosage forms can be prepared.

Powders are prepared quite simply by comminuting the active ingredient to a suitably fine size and mixing with a similarly comminuted diluent. The diluent can be an edible carbohydrate material such as lactose or starch. Advantageously, a sweetening agent or sugar is present as well as a flavoring oil.

Capsules are produced by preparing a powder mixture as hereinafter described and filling into formed gelatin sheaths. Advantageously, as an adjuvant to the filling operation, a lubricant such as talc, magnesium stearate, calcium stearate and the like is added to the powder mixture before the filling operation.

Soft gelatin capsules are prepared by machine encapsulation of a slurry of active ingredients with an acceptable vegetable oil, light liquid petrolatum or other inert oil or triglyceride.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcium phosphate and the like. The powder mixture can be granulated by wetting with a binder such as corn syrup, gelating solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearate salt, talc or mineral oil. The lubricated mixture is then compressed into tablets.

Advantageously, the tablet can be provided with a protective coating consisting of a sealing coat or enteric coat of shellac, a coating of sugar and methylcellulose and a polish coating of carnauba wax.

Fluid unit dosage forms for oral administration such as syrups, elixirs and suspensions can be prepared wherein each teaspoonful of composition contains a predetermined amount of active ingredient for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions the water-soluble active ingredient can be dissolved in water for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization cannot be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

In addition to oral and parenteral administration, the rectal and vaginal routes can be utilized. An active ingredient can be administered by means of a suppository. A vehicle which has a melting point at about body temperature or one that is readily soluble can be utilized. For example, cocoa butter and various polyethylene glycols carbowaxes) can serve as the vehicle.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets teaspoonfuls, tablespoonfuls, dropperfuls, ampules, vials, segregated multiples of any of the foregoing, and other forms as herein described.

The systemic administration of ibuprofen, its salts or esters, to humans provides a useful method of treating ARDS and a means for reducing non-cardiac pulmonary edema and non-cardiac pulmonary hypertension.

The dose of ibuprofen, its salts or esters, for treating ARDS is the same dose known for treating conditions for which it is previously known to be useful. In general, from about 2.5 mg to about 50 mg per kilogram body weight administered daily in single or divided dosage amount.

The following examples are illustrative of the present invention, but are not intended to be limiting.

EXAMPLE 1

Hard Gelatin Capsules

One thousand two-piece hard gelatin capsules for oral use, each capsule containing 100 mg of ibuprofen are prepared from the following types and amounts of ingredients:

| Ibuprofen | 100 gm |
| --- | --- |
| Lactose | 100 gm |
| Corn starch | 20 gm |
| Talc | 20 gm |
| Magnesium stearate | 2 gm |

The ibuprofen finely divided by means of an air micronizer, is added to the other finely powdered ingredients, mixed thoroughly and then encapsulated in the usual manner.

The foregoing capsules are useful for treating ARDS by the oral administration of two capsules four times a day.

Using the procedure above, capsules are similarly prepared containing ibuprofen in 300, 400, and 600 mg amounts by substituting 300, 400, and 600 gm of ibuprofen for the 100 gm used above.

EXAMPLE 2

Soft Gelatin Capsules

One-piece soft gelatin capsules for oral use, each containing 300 mg of ibuprofen (finely divided by means of an air micronizer) are prepared by first suspending the compound in 0.5 ml of corn oil to render the material capsulatable and then capsulating in the above manner.

The foregoing capsules are useful for treating ARDS by the oral administration of two capsules four times a day.

EXAMPLE 3

Tablets

One thousand tablets, each containing 300 mg of ibuprofen are prepared from the following types and amounts of ingredients:

| Ibuprofen micronized | 300 gm |
| --- | --- |
| Lactose | 75 gm |
| Corn Starch | 50 gm |
| Magnesium stearate | 4 gm |
| Light liquid petrolatum | 5 gm |

The ibuprofen (finely divided by means of an air micronizer) is added to the other ingredients and then thoroughly mixed and slugged. The slugs are broken down by forcing through a number sixteen screen. The resulting granules are then compressed into tablets, each tablet containing 300 mg of ibuprofen.

The foregoing tablets are useful for treating ARDS by the oral administration of one or two tablets four times a day.

Using the procedure above, tablets are similarly prepared containing ibuprofen in 400 mg and 600 mg amounts by substituting 400 gm and 600 gm of ibuprofen for the 300 gm used above.

EXAMPLE 4

Oral Suspension

One thousand ml of an aqueous suspension for oral use, containing in each teaspoonful (5 ml) dose, 100 mg of ibuprofen, aluminum salt is prepared from the following types and amounts of ingredients:

| Ibuprofen, Aluminum Salt micronized | 20 gm |
| --- | --- |
| Citric acid | 2 gm |
| Benzoic acid | 1 gm |
| Sucrose | 700 gm |
| Tragacanth | 5 gm |
| Lemon oil | 2 gm |
| Deionized water, q.s. | 1000 ml |

The citric acid, benzoic acid, sucrose, tragacanth and lemon oil are dispersed in sufficient water to make 850 ml of suspension. The ibuprofen aluminum salt (finely divided by means of an air micronizer) is stirred into the syrup until uniformly distributed. Sufficient water is added to make 1000 ml.

The composition so prepared is useful for treating ARDS at a dose of one tablespoonful (15 ml) four times a day.

EXAMPLE 5

A sterile aqueous solution for parenteral (i.v.) injection, containing in one liter, 350 mg of ibuprofen, sodium salt is prepared from the following types and amounts of ingredients:

| Ibuprofen sodium salt | 350 mg |
| --- | --- |
| Water for injection, q.s. | 1000 ml |

To the sterile solution is added sterilized ibuprofen, sodium salt and filled into sterile containers sealed.

The composition so prepared is useful for treating ARDS at a dose of one liter every eight hours.

EXAMPLE 6

Following the precedure of the proceeding Examples 1 through 5, inclusive, compositions are similarly prepared substituting equimolar amounts of the ester, e.g., methyl, ethyl, isopropyl, octyl, or salt, e.g., sodium, potassium, ammonium, for the compound of the examples.

I claim:

1. A process for treating adult respiratory distress syndrome comprisig the systemic administration to a human or animal having adult respiratory distress syndrome of an effective amount of p-isobutylhydratropic acid or an alkyl ester of from 1 to 8 carbon atoms, inclusive, including isomeric forms thereof, or a pharmacologically acceptable salt thereof.

2. The process of claim 1 wherein the compound is p-isobutylhydratropic acid.

* * * * *